(12) United States Patent
Izvozchikov

(10) Patent No.: US 7,872,797 B2
(45) Date of Patent: Jan. 18, 2011

(54) DEVICE FOR PLACING MICROSCOPE SLIDES IN SLIDE TRAYS

(76) Inventor: Ilya Borisovich Izvozchikov, ul. Zhaka Dyuklo, 8-2, St. Petersburg 194223 (RU)

( * ) Notice: Subject to any disclaimer, the term of this patent is extended or adjusted under 35 U.S.C. 154(b) by 368 days.

(21) Appl. No.: 12/083,606

(22) PCT Filed: Oct. 25, 2006

(86) PCT No.: PCT/RU2006/000569

§ 371 (c)(1),
(2), (4) Date: Apr. 15, 2008

(87) PCT Pub. No.: WO2007/049994

PCT Pub. Date: May 3, 2007

(65) Prior Publication Data

US 2009/0116104 A1    May 7, 2009

(30) Foreign Application Priority Data

Oct. 28, 2005   (RU) ............................... 2005134508

(51) Int. Cl.
*G02B 23/00* (2006.01)
*B65G 1/06* (2006.01)

(52) U.S. Cl. .................. 359/368; 359/391; 414/331.17; 414/416.03

(58) Field of Classification Search ................. 359/368, 359/391–397
See application file for complete search history.

(56) References Cited

U.S. PATENT DOCUMENTS 3,902,615 A * 9/1975 Levy et al. ............. 414/331.17
4,367,915 A * 1/1983 Georges ..................... 359/385
4,900,212 A * 2/1990 Mikahara ............... 414/416.03

FOREIGN PATENT DOCUMENTS

| DE | 10164548 | 9/2002 |
| EP | 0104142 | 3/1984 |
| SU | 903248 | 7/1982 |
| SU | 1364263 | 7/1988 |

* cited by examiner

*Primary Examiner*—Thong Nguyen
(74) *Attorney, Agent, or Firm*—Paul Vincent

(57) ABSTRACT

A device for histological research includes at least one container with shelves for slide trays connected to a flexible drive enabling reciprocating vertical motion of the container. The drive comprises a circular drive cable, a motor and at least one pulley. The device also includes a horizontal pusher provided on the working end with a tool for gripping the slide tray and moving it into the working zone outside the container and then back into the container, as well as a slide gripper capable of moving horizontally over the working zone in the direction perpendicular to that of the horizontal pusher.

5 Claims, 2 Drawing Sheets

DEVICE FOR PLACING MICROSCOPE SLIDES IN SLIDE TRAYS

This application is the national stage of PCT/RU2006/000569 filed on Oct. 25, 2006 and also claims Paris Convention priority to RU 2005134508 filed on Oct. 28, 2005.

BACKGROUND OF THE INVENTION

The claimed invention relates to equipment for diagnostics and research, in particular, to devices used for preparation of histological and biological specimens for microscopy. It can be applied in biological and medical laboratories performing microscopic study of cell and tissue samples, especially in those specializing in histological and cytological investigation.

Histological or biological specimens that have been appropriately treated, attached to microscopic slides and stained are then mounted in special media so that an optically homogenous area is created and the specimens are preserved for the time period sufficient for investigation. Canada balsam, polystyrene and styrene co-polymers are a few examples of commonly used optical media. Xylene solution of a mounting medium is applied onto a specimen attached to a slide and the whole is covered with a cover slip. Before the specimen can be submitted for the microscopic investigation, the medium must dry out while the slide is positioned horizontally in order to prevent cover slip displacement or medium leakage. Microscopic slides with mounted specimens are laid out for drying in slide trays. A slide tray is a plastic, wooden, or cardboard tray with rectangular standard slide-sized cells. A slide tray may have 10, 20, or 30 cells arranged in a row or in rows. Slides in slide trays are further submitted for microscopic investigation.

Slides are placed in slide trays manually; this operation is rather labour-consuming and requires attentive personnel. In addition, the slide trays consume a lot of laboratory working space while the slides are being laid out.

To our knowledge, there exist no known devices for arranging microscopic slides in slide trays. A known device manufactured by VisionBioSystems, Australia, can deliver microscopic slides from slide trays lying in a container to the microscope stage and return them back into the slide trays, but it is required that the slides have already been placed in the slide trays.

SUMMARY OF THE INVENTION

The technical result achieved by means of the claimed invention amounts to constructing a device which makes it possible to mechanize the labour-consuming procedure of arranging microscopic slides with mounted specimens in slide trays.

Said technical result is achieved by means of the claimed device for placing microscopic slides in slide trays comprising at least one container with horizontal shelves for slide trays which is capable of reciprocating motion along a vertical guide due to a flexible drive composed of a circular drive rope, a motor and at least one pulley, a horizontal pusher provided on the working end with a tool for gripping the slide tray and propelling it into the working zone outside the container and then back into the container, and a slide gripper capable of moving horizontally over the working zone in the direction perpendicular to that of the horizontal pusher.

Said device may as well include two containers located on the opposite sides of the working zone, the second container being connected to the same drive and capable of reciprocating vertical motion. The drive of the device with two containers may include two additional pulleys, one of which is located over the second container level with the motor, and the other one is located under the second container level with the pulley under the first container.

The slide tray gripper of the horizontal pusher can be either a mechanical latch or a magnetic gripper.

BRIEF DESCRIPTION OF THE DRAWING

The claimed invention can be described with reference to drawings as shown in FIGS. 1-4.

DESCRIPTION OF THE PREFERRED EMBODIMENT

Figure 1:
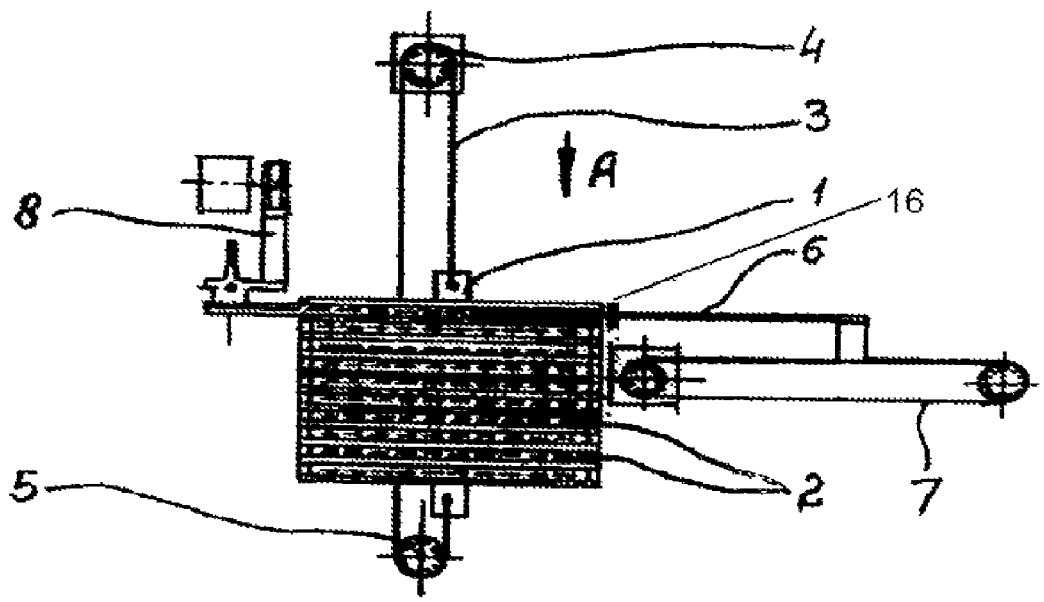
FIG. 1 represents the claimed device including one container with shelves for slide trays.
Figure 2:
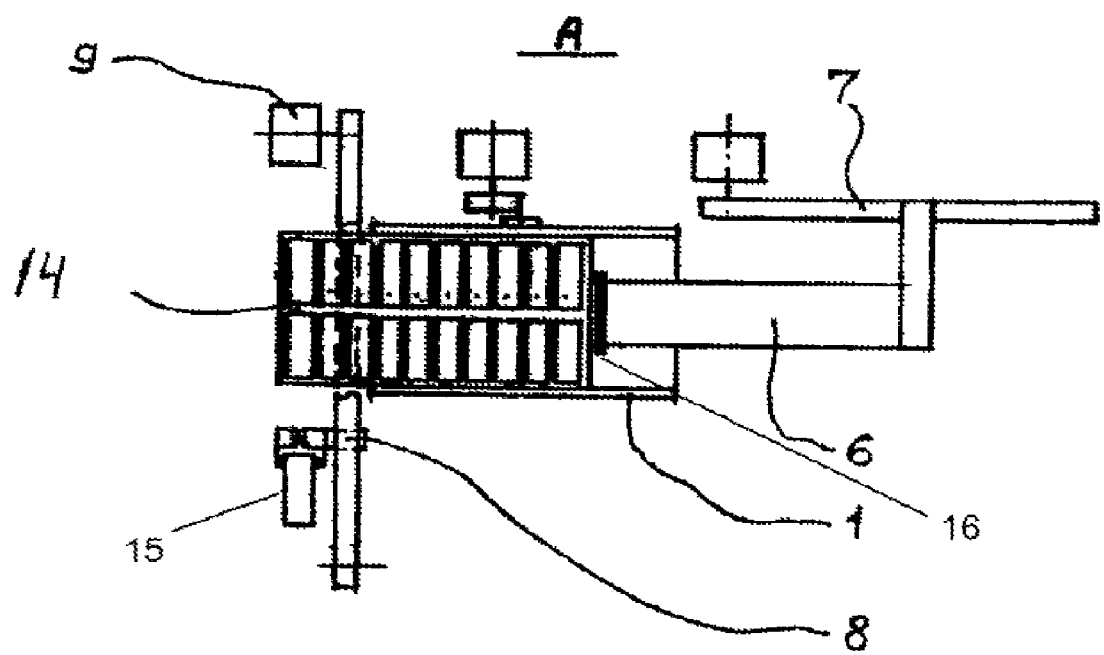
FIG. 2 represents the top view of the same device in the plane of motion of the horizontal pusher.

Container 1 (FIGS. 1, 2) with shelves 2 for slide trays is connected to drive 3, which comprises circular drive rope, motor 4 and pulley 5. The drive rope can be made up of a circular wire or chain, of a flexible metal, rubber, or plastic band, etc. Pusher 6 is connected to drive 7, which enables it of reciprocating motion. At the working end, pusher 6 is provided with a mechanical or magnetic gripper 16 of any kind. In the latter case the slide trays should bear stripes of iron, steel or another magnetic material on the short side. Slide gripper 8 is located over the working zone and capable of moving horizontally in the direction perpendicular to that of the horizontal pusher 6 by means of drive 9 (FIG. 2).

The device may also include a second container 10 (FIGS. 3, 4) with shelves 11 for slide trays, in which case drive 3 includes additional pulleys 12 and 13.

The device functions as follows: Pusher 6 (FIG. 2) propels slide tray 14 into the working zone for one slide-cell width. Gripper 8 moves over the working zone and lays the slide 15 into the cell. Following that, pusher 6 propels slide tray 14 for a further cell width, and gripper 8 places the next slide 15 into its cell. In the event a multi-rowed slide tray 14 is used, slides may either be placed in the tray row by row, or, alternatively, all rows of a column may be filled before the slide tray 14 is pushed forward to the next column.

After slide tray 14 has been filled, pusher 6 returns it to its shelf in container 1. Drive 3 causes container 1 to move for one shelf height so that pusher 6 can actuate the next slide tray 14. (FIG. 1)

Figure 3:
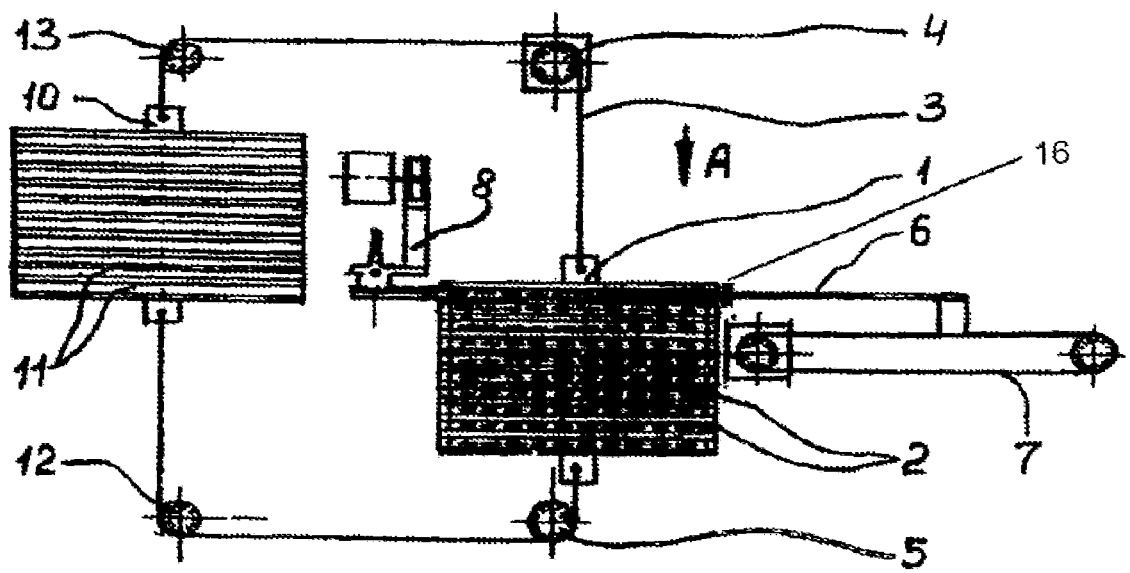
FIG. 3 represents the claimed device including two containers with shelves for slide trays.
Figure 4:
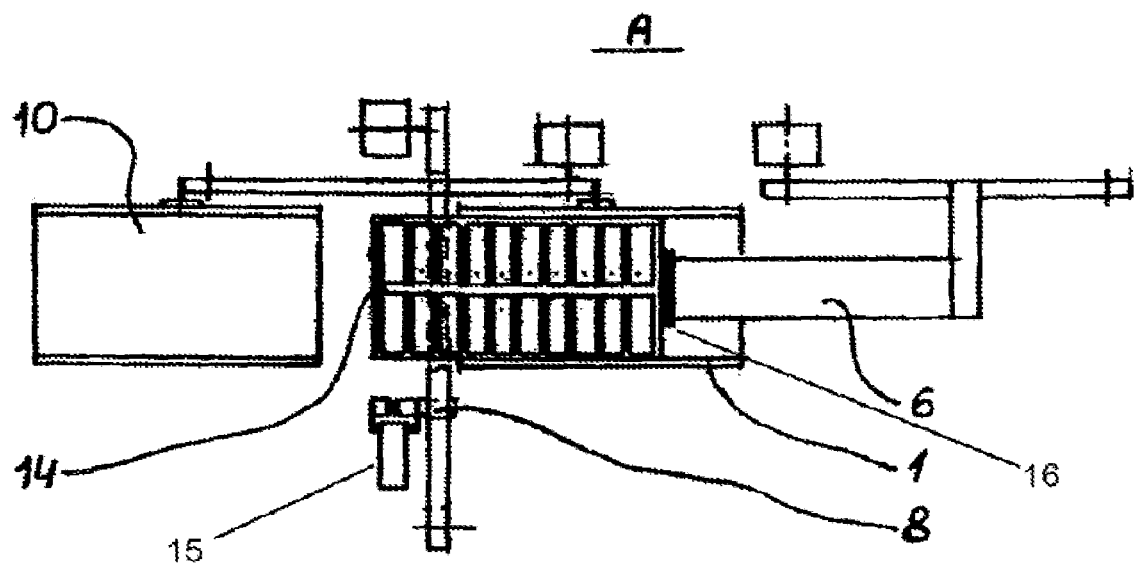
FIG. 4 represents the top view of the device of FIG. 3 in the plane of motion of the horizontal pusher.

The model with two containers is employed as follows (FIGS. 3, 4). Container 1 is loaded with empty slide trays 14; a filled tray 14 is placed on an empty shelf of container 10. Driver 3 causes container 1 to rise and container 10 to descend simultaneously for one step. After container 10 has been filled, loaded slide trays 14 can be removed from it, while container 1 is loaded with empty slide trays 14 another time.

Should the slides 15 be encoded for automated reading by means of microchips, bar code or otherwise, the claimed device can automatically arrange the slides 15 in a specified way. For example, all the slides concerning a particular case can be grouped together. A code-reading input device can be arranged, for example, on gripper 8.

The claimed device for placing microscopic slides into slide trays can be used in histological and cytological laboratories as well as in any other medical and biological institutions performing microscopic investigation of cells and tissues.

The invention claimed is:

1. A device for placing microscope slides on slide trays, the slide trays having multiple cells to accept and arrange the microscope slides in one or more rows, the device comprising:
   - at least one container having horizontal shelves for the slide trays;
   - a flexible drive cooperating with said container, said flexible drive having a circular drive cable rope, a motor, and at least one pulley, said flexible drive structured to effect reciprocating guided motion of said container along a vertical direction;
   - a horizontal pusher having a tool at a working end thereof, said tool structured to grip a slide tray, to displace the slide tray into a working zone outside said container, and to return the slide tray back into said container; and
   - a slide gripper structured for horizontal movement over the working zone in a direction perpendicular to a direction of motion of said horizontal pusher, wherein said drive, said horizontal pusher and said slide gripper are disposed, structured and dimensioned such that said pusher displaces said slide tray into the working zone through one slide-cell width, said gripper moves over the working zone and places a slide into a cell of a corresponding row and said pusher returns said slide tray into said container after filling thereof.

2. The device of claim 1, further comprising a second container having shelves for slide trays, said second container disposed on an other side of the working zone and connected to said flexible drive.

3. The device of claim 2, further comprising two pulleys, one pulley disposed over said second container, level with said motor and an other pulley disposed under said second container, level with a pulley disposed under said container.

4. The device of claim 1, wherein said gripping tool of said horizontal pusher is a mechanical latch.

5. The device of claim 1, wherein said gripping tool of said horizontal pusher is a magnetic gripper.

* * * * *